US009326918B2

(12) United States Patent  
Utterodt et al.

(10) Patent No.: US 9,326,918 B2  
(45) Date of Patent: May 3, 2016

(54) POLYMERIZABLE DENTAL COMPONENTS WITH IMPROVED USAGE PROPERTIES, METHODS FOR ADJUSTING THE USAGE PROPERTIES OF POLYMERIZABLE DENTAL COMPOSITES, AND DENTAL COMPOSITES OPTIMIZED ACCORDING TO SAID METHODS

(71) Applicant: HERAEUS KULZER GMBH, Hanau (DE)

(72) Inventors: Andreas Utterodt, Neu-Anspach (DE); Kurt Reischl, Merenberg (DE); Nelli Schönhof, Braunfels (DE); Michael Eck, Schmitten (DE); Christine Hiersekorn, Dornburg (DE); Jutta Schneider, Runkel (DE)

(73) Assignee: Heraeus Kulzer GmbH, Hanau (DE)

( * ) Notice: Subject to any disclaimer, the term of this patent is extended or adjusted under 35 U.S.C. 154(b) by 0 days.

(21) Appl. No.: 13/799,806

(22) Filed: Mar. 13, 2013

(65) Prior Publication Data

US 2013/0261218 A1    Oct. 3, 2013

(30) Foreign Application Priority Data

Mar. 28, 2012  (DE) .......................... 10 2012 006 152

(51) Int. Cl.
  *G01N 19/00*  (2006.01)
  *G01N 19/04*  (2006.01)
  (Continued)

(52) U.S. Cl.
  CPC ............. *A61K 6/0091* (2013.01); *A61K 6/0047* (2013.01); *G01N 19/00* (2013.01); *G01N 19/04* (2013.01)

(58) Field of Classification Search
  None
  See application file for complete search history.

(56) References Cited

U.S. PATENT DOCUMENTS 3,825,518 A * 7/1974 Sheerness ................. A61K 6/09  
                                                                                                                                             106/35  
4,032,673 A * 6/1977 Schroeter ................. B05D 7/16  
                                                                                                                                             336/219

(Continued)

FOREIGN PATENT DOCUMENTS

EP        1 719 497 A1    11/2006  
EP        2 193 776 A2     6/2010

(Continued)

OTHER PUBLICATIONS

Japanese Examination Report dated Apr. 18, 2014.

*Primary Examiner* — Peter A Salamon  
(74) *Attorney, Agent, or Firm* — Norris McLaughlin & Marcus PA

(57) ABSTRACT

Method for adjusting or improving or optimizing the usage properties of filler(s)-containing, flowable dental material, which involves relating to at least one measuring value representing the tackiness to at least one measuring value representing the texturing or plasticity or consistency. Flowable, usage-optimized, usually non-polymerized dental composites contain, as fillers, at least one glass filler and at least one filler from the group of chipped polymers or pre-polymer fillers based on ground polymer that is pre-polymerized together with inorganic particles, and, as additive(s), at least one compound represented through formula H—Y—Z (I), where:  
Y=—O—, —S—, —CO—, —OSi(OR$^1$)$_2$—, —OE  
Z=H, OH, SH, NH$_2$, COOH, COOR$^2$  
E=—C$_n$H$_m$Op-  
R$^1$=H, C$_1$-C$_4$-Alkyl  
R$^2$=C$_1$-C$_{15}$-Alkyl, interrupted by one or more O atoms. C$_2$-C$_{14}$-Alkyl,  
n=2 bis 5  
m=4 bis 11  
p=n.

16 Claims, 6 Drawing Sheets

(51) Int. Cl.
*A61K 6/00* (2006.01)
*A61K 6/02* (2006.01)
*A61K 6/08* (2006.01)

(56) References Cited

U.S. PATENT DOCUMENTS

| | | | | |
|---|---|---|---|---|
| 5,122,061 | A * | 6/1992 | Wakumoto | C09J 4/00 433/226 |
| 5,773,489 | A * | 6/1998 | Sato | A61K 6/093 106/35 |
| 7,670,580 | B2 * | 3/2010 | Jia | A61K 6/0023 423/335 |
| 7,741,381 | B2 * | 6/2010 | Nakata | A61K 6/0023 433/228.1 |
| 7,879,924 | B2 * | 2/2011 | Torii | A61K 6/0023 106/35 |
| 8,252,851 | B2 * | 8/2012 | Young | A61K 6/033 523/115 |
| 8,292,625 | B2 * | 10/2012 | Skaria | A61K 6/083 433/219 |
| 8,642,679 | B2 * | 2/2014 | Tanaka | A61K 6/0038 523/115 |
| 2004/0063845 | A1 * | 4/2004 | Guzauskas | C08F 291/00 524/494 |
| 2004/0097627 | A1 * | 5/2004 | Vallittu | A61K 6/083 524/430 |
| 2005/0272008 | A1 * | 12/2005 | Stites | A61C 5/00 433/180 |
| 2006/0247330 | A1 * | 11/2006 | Takano | A61K 6/0023 523/116 |
| 2006/0252845 | A1 * | 11/2006 | Ruppert | A61K 6/0091 523/115 |
| 2010/0087565 | A1 * | 4/2010 | Utterodt | A61K 6/0091 523/116 |

FOREIGN PATENT DOCUMENTS

| | | |
|---|---|---|
| JP | 2006299201 A | 11/2006 |
| JP | 2010208964 A | 9/2010 |

* cited by examiner

Fig. 1, Example 4: Effects of the addition of glass filler at constant fraction of pre-polymer filler without additive
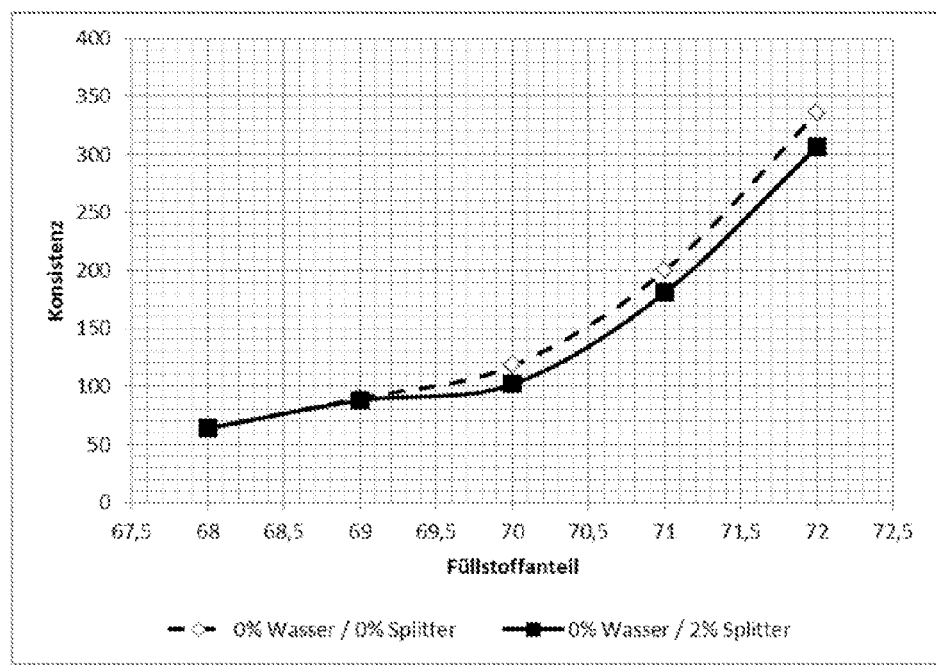
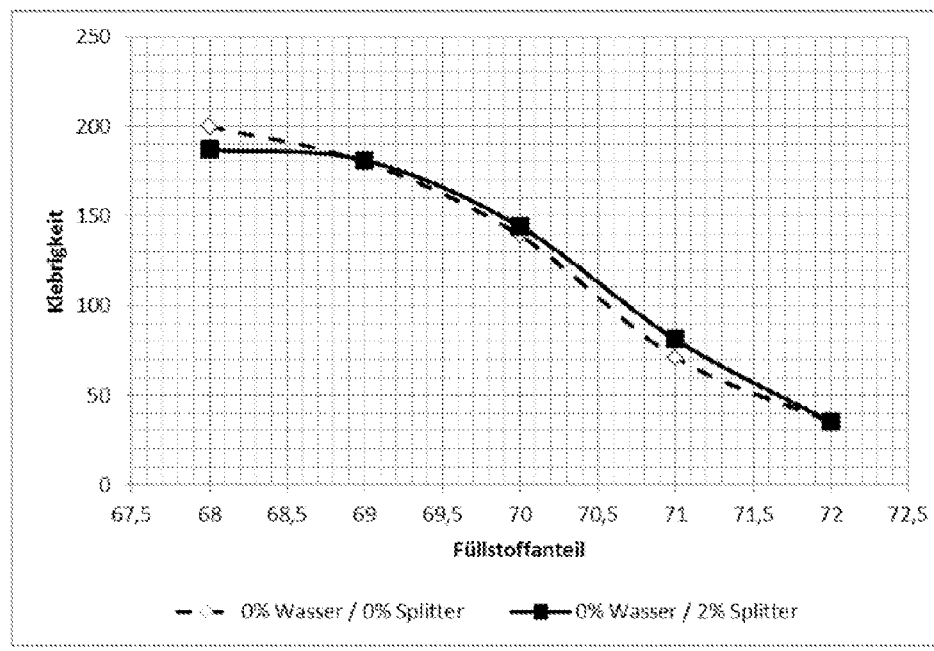

Fig. 2, Example 5: Effects of the addition of glass filler in combination with the addition of water at constant fraction of pre-polymer filler (plot)
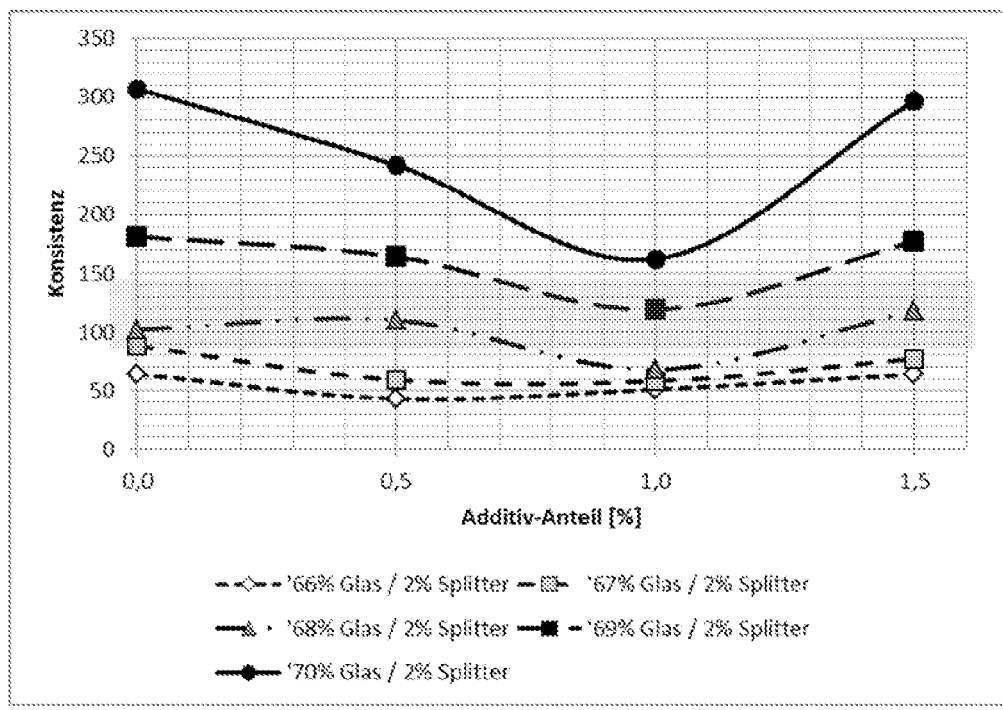
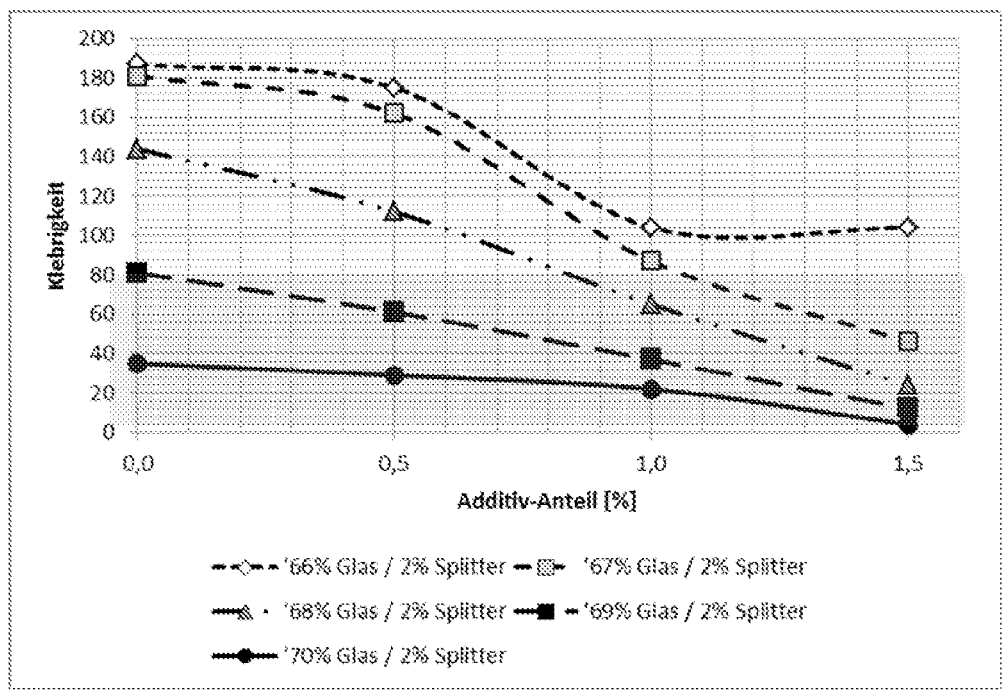

Fig. 3, Example 6: Effects of the addition of pre-polymer filler in combination with the addition of at constant fraction of glass filler (plot)
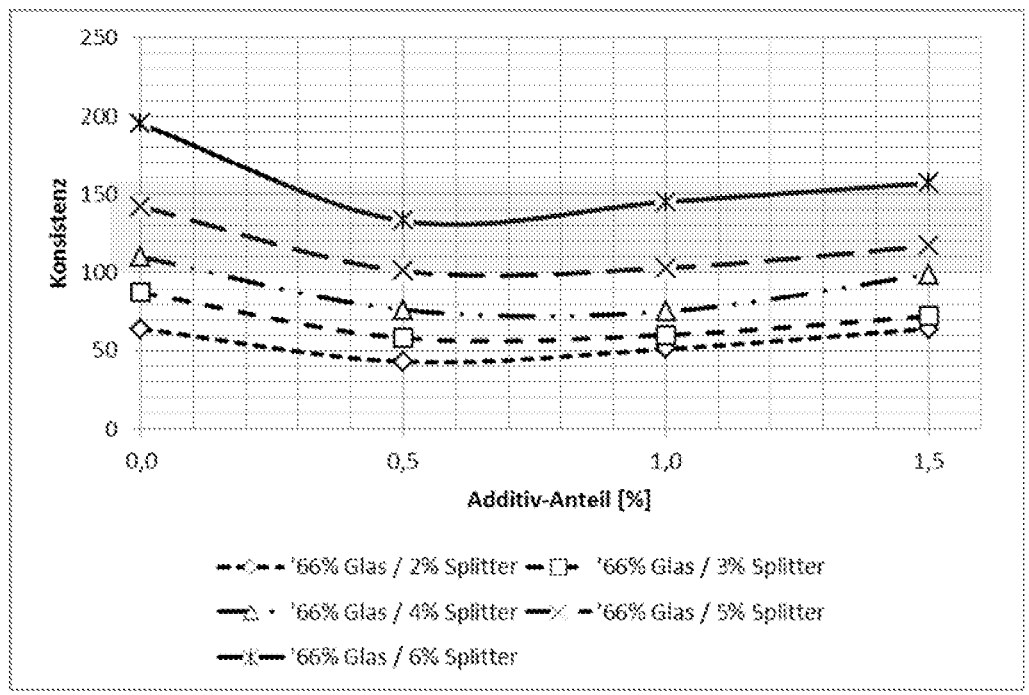
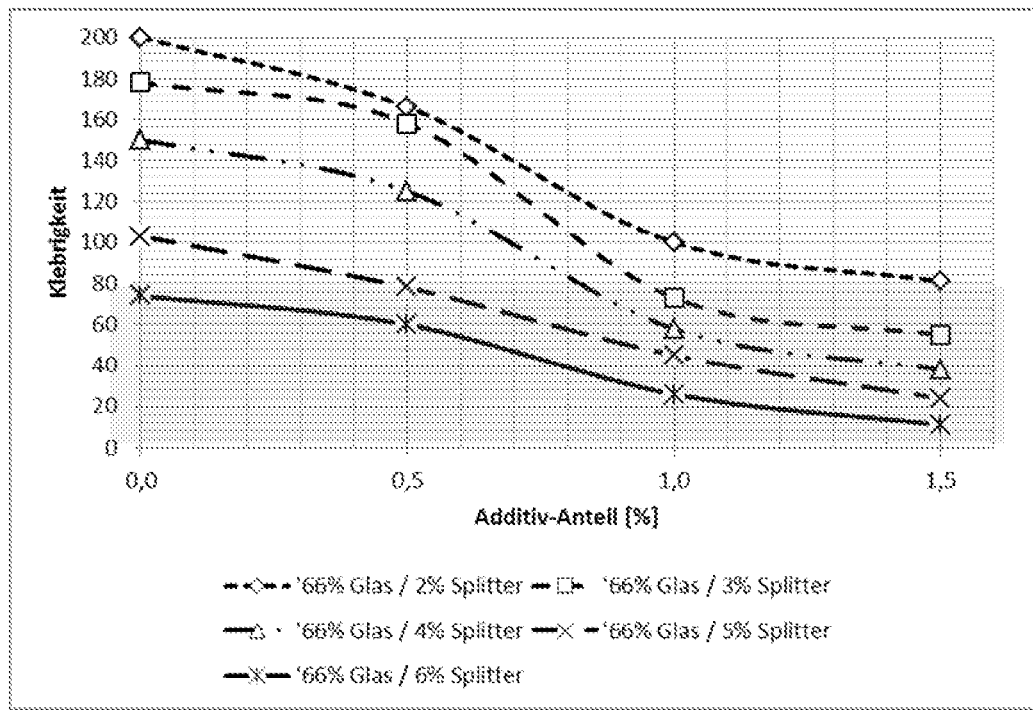

Fig. 4, Example 7: Analysis of the area of optimal plasticity and tackiness by means of the IG/IK ratio (plot)
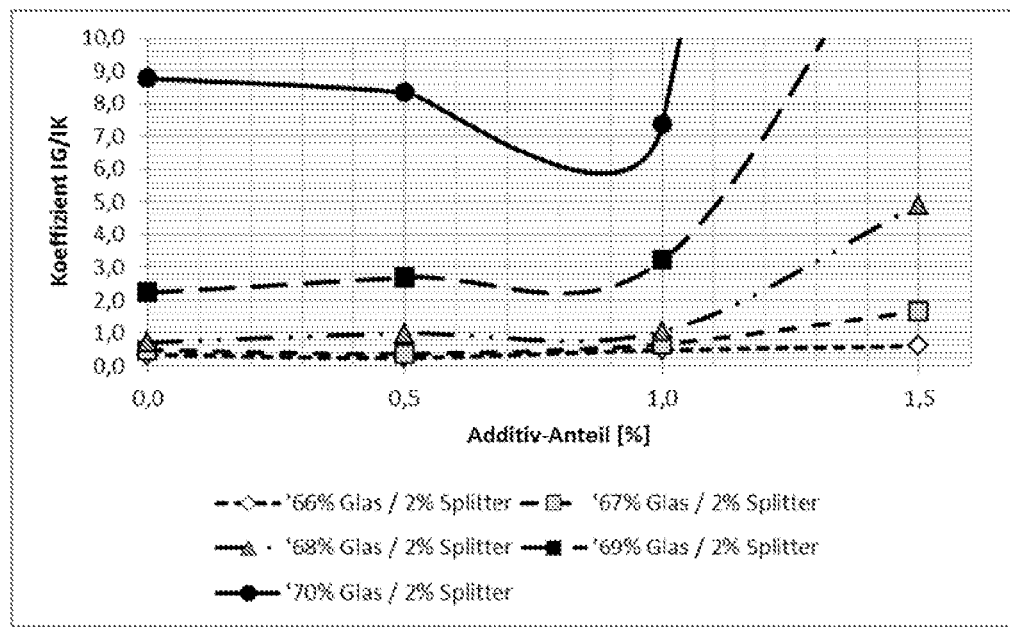
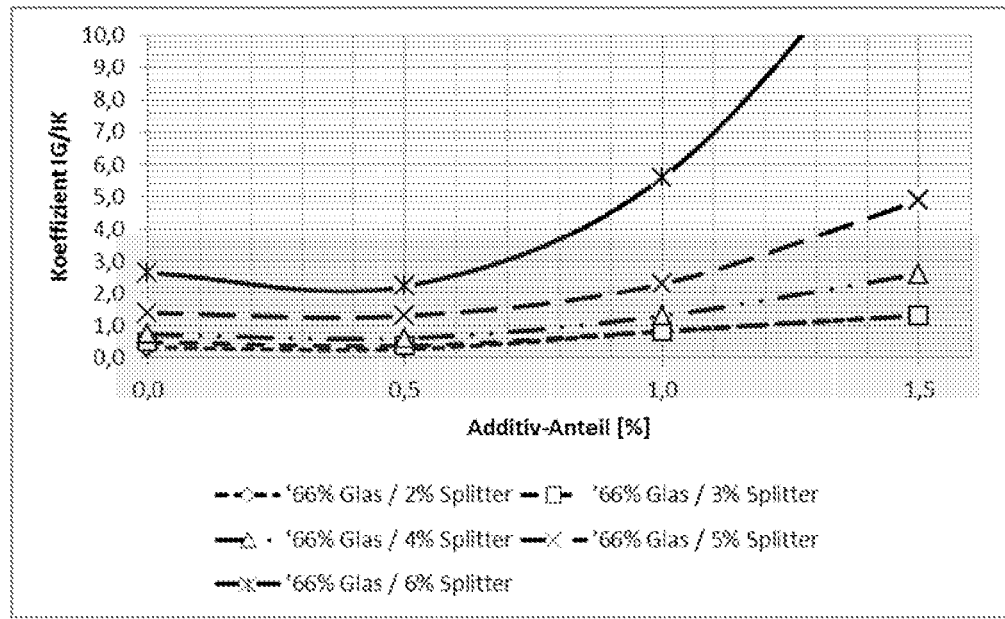

Fig. 5, Example 8: Effects of the addition of glass filler in combination with the addition of additive (PEG200) at constant fraction of pre-polymer filler (plot)
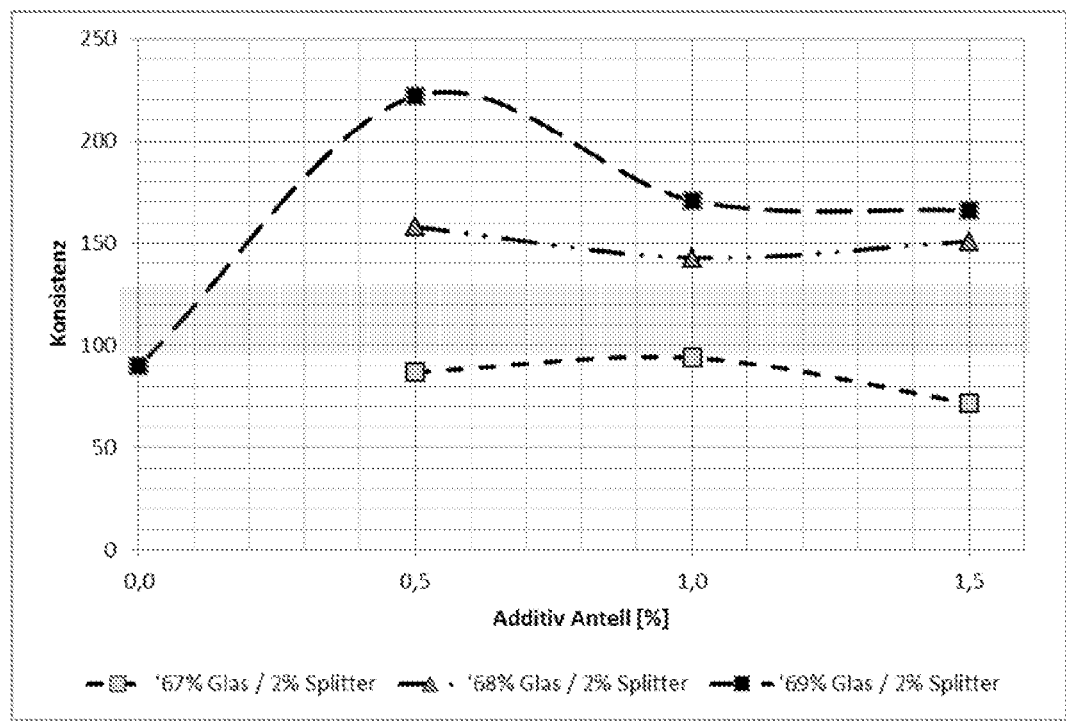
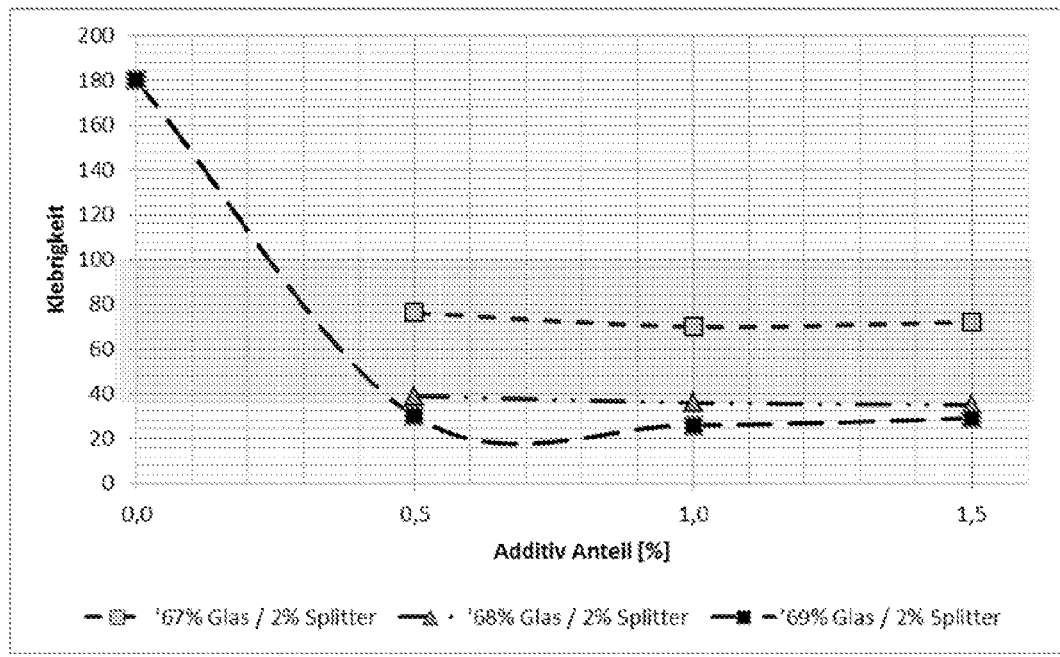

Fig. 6, Example 9: Analysis of the area of optimal plasticity and tackiness by means of the IG/IK ratio (plot)
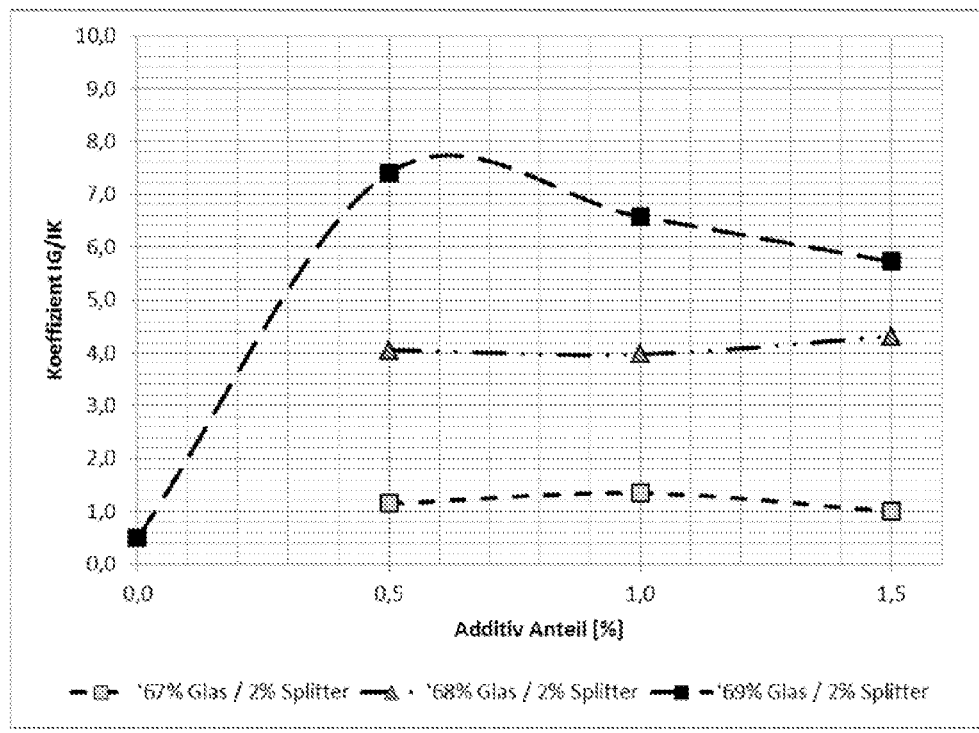

POLYMERIZABLE DENTAL COMPONENTS WITH IMPROVED USAGE PROPERTIES, METHODS FOR ADJUSTING THE USAGE PROPERTIES OF POLYMERIZABLE DENTAL COMPOSITES, AND DENTAL COMPOSITES OPTIMIZED ACCORDING TO SAID METHODS

The invention relates to a novel method for adjusting the usage properties of polymerisable, flowable, usually non-cured dental composites, dental composites with improved or optimised usage properties, in particular dental composites produced according to said method.

BACKGROUND OF THE INVENTION

Numerous dental composites for universal use are known according to the prior art, i.e. dental composites that meet the requirements for restoration of the tooth structure of all cavity classes I, II, III, IV, and V according to G. V. BLACK. From the class of dental composite materials, basically only inorganic-organic hybrid materials with substantial amounts of inorganic fillers, such as dental glass or mineral nano-agglomerates, are suitable for this purpose. Introduced in the 1980s, the micro-filler composites with pre-polymer fillers are not suitable for use in lateral tooth regions (classes I and II) due to their limited resistance to wear (abrasion resistance) and fracture resistance (flexural strength). A high filler content is advantageous in order for the cured composite to attain good mechanical properties and to concurrently reduce the polymerisation shrinkage occurring in the course of the curing process. These properties are also crucial for the long-term success of any therapy involving dental composites.

However, not only the materials properties of a cured dental composite, but also the processing by the user prior to polymerisation is crucial for the long-term success of medical management. The application from the packaging, introduction into the cavity, adaptation to the tooth structure, and shaping of the composite layer are extremely dependent on the plasticity and tackiness of the non-polymerised material. Especially the desired high amounts of inorganic fillers introduce disadvantageous thixotropy into the system due to their surface interactions. Elicited by polar interactions between oxidic filler particles (e.g. silicates), these forces may be disturbed temporarily through shearing, and high shear thinning is characteristic of the composites. The same interactions lead to tackiness on the surface of the composite. Soft composites, in particular, tend to show disadvantageous tackiness since they have better flow properties.

The visco-elastic flow properties are usually determined with rheometers. According to the current prior art, the consistency of composites is corrected solely through slight adjustment of the filler fraction. This is associated with an uncontrolled change of the tackiness. It is still not customary to this day to even measure the tackiness of composites, let alone to adjust it in controlled manner. The product properties therefore vary greatly such that the variation in quality is apparent to the user.

Flowable dental composites are desired to possess certain usage and/or handling properties for dental management or dental lab work pieces involving them to be reliable and successful, i.e. the plasticity not being too firm (sufficient flow properties) and the tackiness (at the application instrument) being low.

SUMMARY OF THE INVENTION

The invention relates to a method for adjusting or improving or optimising the usage properties of dental composites, in particular those having high amounts of filler, through relating and optimising the parameters of texturing and tackiness. The invention also relates to dental composites, in particular dental composites optimised according to said method, that possess improved usage properties in particular in as far as it concerns the parameters of texturing and tackiness. In particular, components A1 and A2 described below are used in the dental composites as additives or part of the filler.

Due to their special composition, dental composites adjusted and/or optimised according to the method of the invention possess an optimal balance of plasticity and tackiness concurrent with very good materials properties. Composites based on the TCD-di-HEA cross-linker have been described to possess outstanding materials properties, in particular low shrinkage at high flexural strength (EP 1 719 497 A1, EP 2 193 776 A2). Urethane cross-linkers (TCD-di-HEA-HEA, HEMA-TMDI) usually form hydrogen bonds and thus lead to higher tackiness and/or firm consistency/plasticity. The preferable soft plasticity in such systems automatically leads to undesired high tackiness.

In order to meet the objective of the invention in terms of substances, it is advantageous to introduce minor fractions of two additional components A1 and A2, no more than 5% by weight, preferably 0.5 to 5% by weight, particularly preferably 1 to 4% by weight.

Component A1: Pre-Polymer Filler

According to current technical expertise, shear thinning decreases upon the addition of pre-polymer fillers, also called chipped polymers or chipped polymer materials, or pre-polymer fillers based on ground polymer that is pre-polymerized together with inorganic particles. However, aside from this known effect, the inventors surprisingly noticed the tackiness at the surface of the composite to be significantly lower (as can be quantified through measuring the peeling force, as described below). Varying the comparably minor fraction of component A1 allows the tackiness to be adjusted over a wide range without effecting major changes in the shear thinning. The mechanical properties remain surprisingly unchanged although the polymer particles are clearly softer.

Component A2: Hydroxy Function-Containing Additives

The addition of liquid hydroxy function-containing additives with a molecular weight of <250 g/mol, preferably corresponding to structural formula (I) shown below, also had a surprising advantageous effect in terms of lowering the plasticity (corresponds to a reduction of shear thinning). This effect is surprising since polar hydroxy function-containing substances are known to increase the interactions and thus the thixotropy. Without wishing to limit the invention through theoretical considerations, the detected effect may be explained in that small molecules may also reduce the existing interactions, presumably through penetrating between existing polar groups and thus by reducing some direct interaction of the surfaces of the particles.

DETAILED DESCRIPTION

Molecules of low molecular weight of this type to be named here are those corresponding to the following formula $$H—Y—Z \qquad (I)$$

where:
Y=—O—, —S—, —CO—, —OSi(OR$^1$)$_2$—, —OE 
Z=H, OH, SH, NH$_2$, COOH, COOR$^2$
E=—C$_n$H$_m$Op-
R$^1$=H, C$_1$-C$_4$-Alkyl $R^2 = C_1$-$C_{15}$-Alkyl, interrupted by one or more O atoms.
$C_2$-$C_{14}$-Alkyl,
n=2 bis 5
m=4 bis 11
p=n.

$C_1$-$C_{15}$ alkyl can be linear or branched and, for example, corresponds to methyl, ethyl, propyl, isopropyl, butyl, isobutyl, sec.-butyl, tert.-butyl, pentyl, isopentyl, hexyl, heptyl, octyl, nonyl, decyl, dodecyl or pentadecyl. $C_1$-$C_{12}$ alkyl, e.g. $C_1$-$C_8$ alkyl or $C_1$-$C_6$ alkyl, in particular $C_1$-$C_4$ alkyl are preferred. $C_1$-$C_{12}$ alkyl, $C_1$-$C_8$ alkyl, $C_1$-$C_6$ alkyl can have the same definitions as specified above, including the corresponding number of C atoms.

$C_2$-$C_{14}$ alkyl interrupted through one or more O atoms is interrupted through —O—, for example, 1 to 5 times, e.g. 1 to 3 times or 1 or 2 times. This results in structural units such as, for example, —O(CH$_2$)$_2$OH, —O(CH$_2$)$_2$OCH$_3$, —O(CH$_2$CH$_2$O)$_2$CH$_2$CH$_3$, —CH$_2$—O—CH$_3$, —CH$_2$CH$_2$—O—CH$_2$CH$_3$, —[CH$_2$CH$_2$O]$_y$—CH$_3$, where y=1 to 5, —(CH$_2$CH$_2$O)$_5$CH$_2$CH$_3$, —CH$_2$—CH(CH$_3$)—O—CH$_2$—CH$_2$CH$_3$ or —CH$_2$—CH(CH$_3$)—O—CH$_2$—CH$_3$.

Examples of preferred compounds of this type having a low molecular weight of less than 250 are, aside from water, low-molecular alcohols, such as ethanol, propanol, isopropanol, n-butanol, multi-valent alcohols, e.g. glycols, such as ethylene glycol, glycerol or polyethylene glycols, and also silanes having methacrylic function(s).

Ethanol, glycerol, polyethylene glycol 200 and silanes having methacrylic function(s) such as, e.g., gamma-(methacryloxy)-propyl-trimethoxysilane (CAS-Number: 2530-85-0) also known as "MEMO" or "Silane A174", as well as water are particularly preferred.

The method according to the invention can also be used to adjust the properties of existing formulations or it can be used in the development of new formulations. Expediently, one starts from known dental composites with a high amount of filler. In this context, the method according to the invention aims to adjust and/or improve or optimise the usage properties. The practical procedure in one possible embodiment of the method is described in more detail in the following:

To start, the filler system was modified based on a known dental composite, e.g. VENUS Diamond® (Heraeus Kulzer) containing TCD-di-HEA[1] as the main cross-linker. The broad particle size distribution of said material, which is advantageous for high filler packing density and excellent mechanical properties, was converted to produce a narrow particle size distribution around ylene glycol (PEG) of MG<250 and glycerol, are known to exert an effect on the rheological properties of composites. The actual influence on and/or their targeted use in non-polymerised composites has neither been investigated systematically nor made use of as of yet.

Based on expert knowledge, increasing polarity in the system should in general lead to an increase in thixotropy. Especially the silicate surfaces of common marketed dental glasses are known in terms of their chemistry and form additional hydroxyl groups by adding water which, according to expert, leads to thixotropy. This effect is also detectable in dental composites, in particular upon minor water uptake of the dry glass material. Although the dental glass particles used are being silanised for use, some effect of thixotropy remains clearly detectable. After the initial water uptake (adsorption to the surface of the glass particles) follows a surprising reversal of this effect leading to marked reduction of the shear thinning. In this context, the expected formation of separate phases does not occur up to a water uptake of approx. 3 to 4% in the tested cases. The water fraction has no adverse effect on the polymerisation of the composites.

Dental composites with high amounts of filler usually contain 60 to 90% by weight of filler.

A dental composite that is preferred in the scope of the invention contains the following components:
65 to 75% by weight glass filler, preferably BaAl-silicate glass
1 to 5% chipped polymer
0.1 to 5% by weight additive represented through formula H—Y—Z
15 to 25% by weight monomer mixture, preferably urethane (meth)acrylates
15 to 20% by weight cross-linker, preferably from the group of TCD-di-HEA and HEMA-TMDI.

Said composites are preferably produced or optimised according to the method according to the invention or they are obtained through improvement of existing formulations.

The usage properties of a composite are a complex interaction of thixotropy, shear thinning, and tackiness. Said properties can also be an important success factor for restorative therapy and can be adjusted appropriately using the method according to the invention.

For safe assessment of said effects, test methods have been developed for detecting the properties of the composites (flow properties/shear thinning, and tackiness) through actual measurements.

The texture is determined, e.g., through measuring the flowability. A standard shear test precedes the measurement

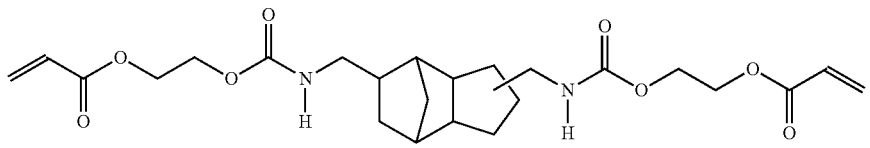

a mean of 1 to 2 μm. The lower packing density and reduced filler surface area is to enable better flowability (lower shear thinning). The ensuing higher shrinkage of the composite was improved through adding a significantly larger-sized pre-polymer filler (mean particle size approx. 30 μm). Surprisingly, minor fractions of pre-polymer filler have no disadvantageous effects on the mechanical properties, but lower the tackiness very markedly.

In general, small polar molecules, such as the compounds summarised through formula I, such as, e.g. water, polyethsuch that the condition of the composite during processing and after extrusion from the packaging is being simulated. Then, the consistency of the composite is determined—for example through having it penetrate through a defined needle (probe) at a defined penetration rate and utilising the resistance force (corresponds to a weight force) (the consistency can be determined at rest without preparatory shearing, but this is of little relevance for the practice of processing). The result is a numerical value IG (corresponding to a weight force) that is listed in the tables and diagrams of the examples.

The tackiness (initial tackiness) is determined through measuring the force needed for peeling off the surface of the composite. In this context, a test stamp made of metal is placed on the prepared material and peeled off in a defined manner measuring the force of adhesion. The result is a numerical value IK (corresponding to a weight force) that is listed in the tables and diagrams of the examples. This value is plotted over the IG value in the diagrams.

In addition, the development of the method according to the invention also included an empirical quality assessment: The corresponding composite materials were subjected to a test under real-life conditions and their usage properties were assessed by the users (dental technicians and dentists) as good, moderate or poor. The mixtures assessed to be particularly well-suited and/or acceptable are identified in the tables of the examples through ! and *, respectively. Mixtures assessed to be poorly suitable or fully unsuitable are identified through • and Ø, respectively.

Accordingly, it was found that compositions shown to possess advantageous usage properties had IG/IK ratios of 2-5, particularly advantageous ones had a ratio of 2-3. This empirical base allows the type of additive to be optimised and the quantitative fraction of the composition accounted by them as well as the optimal quantitative ratio of glass filler and chipped polymer to be determined (see example 7).

By implication, this means that the usage properties can be predicted after determination of the IK and IG values. The person skilled in the art is thus furnished with a tool for specifically influencing the usage properties without having to resort to trial and error. The scope of tests under real-life conditions can therefore be reduced greatly through application of the method according to the invention.

The term, "flowable dental composite", as used herein is preferably understood to mean a deformable material, though not necessarily an inviscid dental material. In particular, the degree of "flowability" of suitable materials is generally determined in that measuring methods for firmness/consistency and tackiness are applicable.

Initial Tackiness

This measurement determines the tackiness (adhesion force), in grams, needed to peel off a measuring stamp that is pressed onto the sample with a defined force.

Rigidity

This measurement determines the opposing force, in grams, at a predetermined penetration depth of a measuring stamp.

The invention is illustrated in more detail through the following examples. All specifications of parts and percentages refer to the weight unless specified otherwise.

EXAMPLES

A number of variants of composites were produced. One of these (containing no chipped polymer) consists of the following components: 1% TEGDMA, 6% HEMA-TMDI, 15% TCD-di-HEA, 6% $SiO_2$, 72% dental glass. The components not specified explicitly in the compositions in the tables are evident from this information.

The variants of composites that are evident from the tables were tested according to the invention for tackiness and flow properties. The latter was determined by means of the rigidity. The procedure is as follows:

Samples:
Samples of the paste mixture to be tested, freshly homogenised using a centrifugal mixer.
Ambient Conditions:
Measuring room with defined climatic conditions.

Example A

Test of Initial Tackiness of Highly Viscous Pastes

This measurement determines the tackiness (adhesion force), in grams, needed to peel off a measuring stamp that is pressed onto the sample with a defined force.
Equipment:
Force-distance measuring unit with defined test stamp
The measuring stamp is placed under defined conditions on the sample freshly homogenised with a centrifugal mixer, and the force required to peel it off is determined. The result specified here is the mean of the adhesive force in pond or gram [g].

Example B

Test of Rigidity of Highly Viscous Pastes

This measurement determines the opposing force, in grams, at a predetermined penetration depth of a measuring stamp.
Equipment:
Force-distance measuring unit with defined test stamp.
The result specified here is the mean of the force in pond or gram [g].

Examples 1, 2, and 3

Consideration of the Assessment from Real-Life Test

The IG and IK values obtained as described above and the results of the user assessment in real-life tests (symbols !, *, •, Ø mean optimised, acceptable, poorly suitable, and not suitable, respectively) are summarised using variations of the formulation of the VENUS Diamond® dental composite (Heraeus Kulzer GmbH; Business Unit Dentistry—Heraeus Dental) in Example 1, Table 1, as an example.

The calculated IG/IK values are labelled with symbols, ∞ poorly suitable, * acceptable, and ! released (or to be considered optimised).

The individual tables of example 2 show compositions with various glass and chipped polymer pre polymer fill fractions and an increasing water content, whereby the water was added in defined amounts as an additive. The results of assessment of the usage properties are again labelled with symbols !, *, •, and Ø.

In analogy to example 1, example 3 shows the influence of additives PEG and MEMO.

The relationships between the tackiness and texturing values determined again illustrate the scientific approach to the optimisation of dental composites. They are summarised in the diagrams of the figures:

BRIEF DESCRIPTION OF THE DRAWINGS

FIG. 1 (example 4) shows the consistency and tackiness profile for the addition of glass filler and a constant fraction of pre-polymer filler without additive.

FIG. 2 (example 5) shows the effect of water as an additive under the conditions of example 4.

FIG. 3 (example 6) shows the effects of varying the pre-polymer filler fraction and the water fraction at constant glass filler fraction.

FIG. 4 (example 7) shows how the optimal conditions can be determined from examples 5 and 6 through plotting the IG/IK values.

FIG. 5 (example 8) shows the consistency and tackiness profile for the addition of glass filler and a constant fraction of pre-polymer filler without and with 3 different amounts of the MEMO additive.

FIG. 6 (example 9) shows the analysis of example 8 through plotting the IG/IK values.

ABBREVIATIONS i) F %=Filler fraction, in % (mass fraction of all fillers: dental glass and pre-polymer)
ii) SD=Standard deviation
iii) GRM=Base mass (composite material without colour-conveying pigmentation)
iv) o.=no
v) Std.=Standard
vi) Splitter=Pre-polymer filler
vii) HEMA=2-Hydroxyethylmethacrylate
viii) TMDI=2,2,4(2,4,4)-Trimethyl-1,6-hexanediisocyanate
ix) HEMA/TMDI=Addition reaction product from vii and viii
x) TEGDMA=Triethylene glycol dimethacrylate
xi) TCD-di-HEA=(Bis-(acryloyloxymethyl)tricyclo[5.2.1.02,6]decane)

Example 1

Influence of Additive Water—Measuring Values/Assessments

Measuring results Textures Analyses

| Name of material | Comment | Water [%] | Pre-polymer [%] | Glass [%] | F % | IG Force, g | SD | IK Force, g | SD | Comments Acceptance range | IG 110-170 | Coefficient IG/IK 1.25-5.6 |
|---|---|---|---|---|---|---|---|---|---|---|---|---|
| SOCO GRM | | | | | | 120-170 | | 30-100 | | Release range | 125-160 | 1.7-4.16 |
| SOCO GRM VP 050711 KR1 | no H₂O - Std. Paste | 0 | 2 | 66 | 68 | 64• | 3 | 187 Ø | 6 | | 64 | 0.3∞ |
| SOCO GRM VP 050711 KR1/K1 | | 0 | 2 | 67 | 69 | 88• | 4 | 181 Ø | 7 | | 88 | 0.5∞ |
| SOCO GRM VP 050711 KR1/K2 | | 0 | 2 | 68 | 70 | 102• | 2 | 144 Ø | 7 | | 102 | 0.7∞ |
| SOCO GRM VP 050711 KR1/K3 | | 0 | 2 | 69 | 71 | 181 Ø | 7 | 81! | 7 | | 181 | 2.2! |
| SOCO GRM VP 050711 KR1/K4 | | 0 | 2 | 70 | 72 | 307 Ø | 6 | 35! | 4 | | 307 | 8.8∞ |
| SOCO GRM VP 140611 KR2 | no H₂O/G 018-053 | 0 | 0 | 68 | 68 | 64• | 2 | 200 Ø | 6 | | 64 | 0.3∞ |
| SOCO GRM VP 140611 KR2/K1 | | 0 | 0 | 69 | 69 | 90• | 4 | 180 Ø | 12 | | 90 | 0.5∞ |
| SOCO GRM VP 140611 KR2/K2 | | 0 | 0 | 70 | 70 | 118• | 4 | 139 Ø | 9 | | 118 | 0.8∞ |
| SOCO GRM VP 140611 KR2/K3 | | 0 | 0 | 71 | 71 | 200 Ø | 3 | 71! | 6 | | 200 | 2.8! |
| SOCO GRM VP 140611 KR2/K4 | | 0 | 0 | 72 | 72 | 336 Ø | 13 | 35! | 3 | | 336 | 9.6∞ |
| SOCO GRM VP 140611 KR2 | no H₂O/ Splitter | 0 | 2 | 66 | 68 | 64• | 2 | 200 Ø | 6 | | 64 | 0.3∞ |
| SOCO GRM VP 140611 KR2/SP/K1 | | 0 | 3 | 66 | 69 | 87• | 3 | 178 Ø | 6 | | 87 | 0.5∞ |
| SOCO GRM VP 140611 KR2/SP/K2 | | 0 | 4 | 66 | 70 | 110• | 1 | 150 Ø | 8 | | 110 | 0.7∞ |
| SOCO GRM VP 140611 KR2/SP/K3 | | 0 | 5 | 66 | 71 | 142! | 5 | 103 Ø | 5 | | 142 | 1.4* |
| SOCO GRM VP 140611 KR2/SP/K4 | | 0 | 6 | 66 | 72 | 195 Ø | 6 | 74! | 3 | | 195 | 2.6! |
| SOCO GRM VP 140611 KR3 | 0.5% H₂O/G 018-053 UF | 0.5 | 2 | 66 | 68 | 44• | 1 | 175 Ø | 10 | | 44 | 0.3∞ |
| SOCO GRM VP 140611 KR3/K1 | | 0.5 | 2 | 67 | 69 | 59• | 2 | 162 Ø | 11 | | 59 | 0.4∞ |
| SOCO GRM VP 140611 KR3/K2 | | 0.5 | 2 | 68 | 70 | 110• | 3 | 112 Ø | 12 | | 110 | 1.0∞ |
| SOCO GRM VP 140611 KR3/K3 | | 0.5 | 2 | 69 | 71 | 164! | 8 | 61! | 5 | | 164 | 2.7! |
| SOCO GRM VP 140611 KR3/K4 | | 0.5 | 2 | 70 | 72 | 242 Ø | 7 | 29 | 3 | | 242 | 8.3∞ |
| SOCO GRM VP 140611 KR3 | 0.5% H₂O/ Splitter | 0.5 | 2 | 66 | 68 | 44• | 1 | 175 Ø | 10 | | 44 | 0.3∞ |
| SOCO GRM VP 200611 KR1 | 0.5% H₂O/ Splitter | 0.5 | 2 | 66 | 68 | 43• | 2 | 166 Ø | 10 | | 43 | 0.3∞ |
| SOCO GRM VP 200611 KR1/SP/K1 | | 0.5 | 3 | 66 | 69 | 58• | 3 | 158 Ø | 8 | | 58 | 0.4∞ |
| SOCO GRM VP 200611 KR1/SP/K2 | | 0.5 | 4 | 66 | 70 | 76• | 3 | 125 Ø | 5 | | 76 | 0.6∞ |
| SOCO GRM VP 200611 KR1/SP/K3 | | 0.5 | 5 | 66 | 71 | 101• | 3 | 78! | 3 | | 101 | 1.3* |

-continued

| | | | | | | | | | | | |
|---|---|---|---|---|---|---|---|---|---|---|---|
| | | | | | | | | | | | Coefficient |
| | | Water | Pre-polymer | Glass | | IG Force, | | IK Force, | | Comments | IG | IG/IK |
| Name of material | Comment | [%] | [%] | [%] | F % | g | SD | g | SD | Acceptance range | 110-170 | 1.25-5.6 |
| SOCO GRM VP 200611 KR1/SP/K4 | | 0.5 | 6 | 66 | 72 | 133! | 3 | 60! | 2 | | 133 | 2.2! |
| SOCO GRM VP 270611 KR | 1.0% H₂O/G 018-053 UF | 1 | 2 | 66 | 68 | 50• | 1 | 104 Ø | 9 | | 50 | 0.5∞ |
| SOCO GRM VP 270611 KR/K1 | | 1 | 2 | 67 | 69 | 58• | 2 | 87! | 8 | | 58 | 0.7∞ |
| SOCO GRM VP 270611 KR/K2 | | 1 | 2 | 68 | 70 | 68• | 2 | 65! | 4 | | 68 | 1.0∞ |
| SOCO GRM VP 270611 KR/K3 | | 1 | 2 | 69 | 71 | 119• | 4 | 37! | 1 | | 119 | 3.2! |
| SOCO GRM VP 270611 KR/K4 | | 1 | 2 | 70 | 72 | 162! | 5 | 22 | 7 | | 162 | 7.4∞ |
| SOCO GRM VP 220611 KR. | 1.0% H₂O/ Splitter | 1 | 2 | 66 | 68 | 51• | 2 | 100! | 12 | | 51 | 0.5∞ |
| SOCO GRM VP 220611 KR/SP/K1 | | 1 | 3 | 66 | 69 | 60• | 2 | 73! | 5 | | 60 | 0.8∞ |
| SOCO GRM VP 220611 KR/SP/K2 | | 1 | 4 | 66 | 70 | 75• | 2 | 58! | 5 | | 75 | 1.3* |
| SOCO GRM VP 220611 KR/SP/K3 | | 1 | 5 | 66 | 71 | 103• | 2 | 45! | 5 | | 103 | 2.3! |
| SOCO GRM VP 220611 KR/SP/K4 | | 1 | 6 | 66 | 72 | 145! | 4 | 26 | 4 | | 145 | 5.6* |
| SOCO GRM VP300611 KR | 1.5% H₂O/G 018-053 UF | 1.5 | 2 | 66 | 68 | 56• | 3 | 93! | 10 | | 56 | 0.6∞ |
| SOCO GRM VP300611 KR/K1 | | 1.5 | 2 | 67 | 69 | 77• | 2 | 46! | 4 | | 77 | 1.7* |
| SOCO GRM VP300611 KR/K2 | | 1.5 | 2 | 68 | 70 | 118• | 1 | 24 | 4 | | 118 | 4.9* |
| SOCO GRM VP300611 KR/K3 | | 1.5 | 2 | 69 | 71 | 177 Ø | 3 | 12 | 1 | | 177 | 14.8∞ |
| SOCO GRM VP300611 KR/K4 | | 1.5 | 2 | 70 | 72 | 297 Ø | 9 | 4 | 1 | | 297 | 74.3∞ |
| SOCO GRM VP 040711 KR1 | 1.5% H₂O/ Splitter | 1.5 | 2 | 66 | 68 | 64• | 5 | 81! | 9 | | 64 | 0.8∞ |
| SOCO GRM VP 040711 KR1/SP/K1 | | 1.5 | 3 | 66 | 69 | 72• | 3 | 55! | 3 | | 72 | 1.3* |
| SOCO GRM VP 040711 KR1/SP/K2 | | 1.5 | 4 | 66 | 70 | 99• | 3 | 38! | 3 | | 99 | 2.6! |
| SOCO GRM VP 040711 KR1/SP/K3 | | 1.5 | 5 | 66 | 71 | 117• | 2 | 24 | 3 | | 117 | 4.9* |
| SOCO GRM VP 040711 KR1/SP/K4 | | 1.5 | 6 | 66 | 72 | 157! | 3 | 11 | 1 | | 157 | 14.3∞ |
| SOCO GRM VP 270611 KR/K1 | 1.0% H₂O/ Splitter | 1 | 2 | 67 | 69 | 58• | 2 | 87! | 8 | | 58 | 0.7∞ |
| SOCO GRM VP 160811 Rei1 FK67/3 1% H2O | | 1 | 3 | 67 | 70 | 92• | 3 | 38! | 3 | | 92 | 2.4! |
| SOCO GRM VP 160811 Rei2 FK67/4 1% H2O | | 1 | 4 | 67 | 71 | 135 | 3 | 27 | 1 | | 135 | 5.0* |
| SOCO GRM VP 170811 Rei1 FK67/5 1% H2O | | 1 | 5 | 67 | 72 | 187 Ø | 2 | 7 | 2 | | 187 | 26.7∞ |
| SOCO GRM VP 170811 Rei2 FK67/6 1% H2O | | 1 | 6 | 67 | 73 | 265 Ø | 9 | 3 | 1 | | 265 | 88.3∞ |
| SOCO GRM VP 270611 KR/K2 | 1.0% H₂O/ Splitter | 1 | 2 | 68 | 70 | 68• | 2 | 65! | 4 | | 68 | 1.0∞ |
| SOCO GRM VP 170811 Rei2 FK68/3 1% H2O | | 1 | 3 | 68 | 71 | 178 Ø | 4 | 14 | 3 | | 178 | 12.7∞ |
| SOCO GRM VP 180811 Rei2 FK68/4 1% H2O | | 1 | 4 | 68 | 72 | 208 Ø | 5 | 11 | 2 | | 208 | 18.9∞ |
| SOCO GRM VP 140611 KR3/K1 | 0.5% H₂O/ Splitter | 0.5 | 2 | 67 | 69 | 59• | 2 | 162 Ø | 11 | | 59 | 0.4∞ |
| SOCO GRM VP 180811 Rei2 FK63/3 0.5% H2O | | 0.5 | 3 | 67 | 70 | 92• | 2 | 115 Ø | 9 | | | |
| SOCO GRM VP 180811 Rei3 FK67/4 0.5% H2O | | 0.5 | 4 | 67 | 71 | 130! | 4 | 60! | 3 | | 130 | 2.2! |

-continued

| | | | | | | | | | | | |
|---|---|---|---|---|---|---|---|---|---|---|---|
| | | | Measuring results Textures Analyses | | | | | | | | |
| Name of material | Comment | Water [%] | Pre-polymer [%] | Glass [%] | F % | IG Force, g | SD | IK Force, g | SD | Comments Acceptance range | IG 110-170 | Coefficient IG/IK 1.25-5.6 |
| SOCO GRM VP 190811 Rei1 FK67/5 0.5% H2O | | 0.5 | 5 | 67 | 72 | 167! | 3 | 27 | 3 | | 167 | 6.2∞ |
| SOCO GRM VP 140611 KR3/K2 | 0.5% H₂O/ Splitter | 0.5 | 2 | 68 | 70 | 110• | 3 | 112 Ø | 12 | | 110 | 1.0∞ |
| SOCO GRM VP 190811 Rei2 FK68/3 0.5% H2O | | 0.5 | 3 | 68 | 71 | 132! | 2 | 57! | 1 | | 132 | 2.3! |
| SOCO GRM VP 190811 Rei3 FK68/4 0.5% H2O | | 0.5 | 4 | 68 | 72 | 194 Ø | 1 | 28 | 1 | | 194 | 6.9∞ |

Example 2

Influence of Additive Water—Matrix Analysis

| | | | | Glass | | | | |
|---|---|---|---|---|---|---|---|---|
| IG | | 66 | 67 | 68 | 69 | 70 | 71 | 72 |
| | 0% water | | | | | | | |
| Splitter | 0 | | | 64• | 90• | 118• | 200 Ø | 336 Ø |
| | 2 | 64• | 88• | 102• | 181 Ø | 307 Ø | | |
| | 3 | 87• | | | | | | |
| | 4 | 110• | | | | | | |
| | 5 | 142! | | | | | | |
| | 6 | 195 Ø | | | | | | |
| | 0.5% water | | | | | | | |
| Splitter | 0 | | | | | | | |
| | 2 | 43• | 59• | 110• | 164! | 242 Ø | | |
| | 3 | 58• | 92• | 132! | | | | |
| | 4 | 76• | 130! | 194 Ø | | | | |
| | 5 | 101• | 167! | | | | | |
| | 6 | 133! | | | | | | |
| | 1% water | | | | | | | |
| Splitter | 0 | | | | | | | |
| | 2 | 50• | 58• | 68• | 119• | 162! | | |
| | 3 | 60• | 92• | 178 Ø | | | | |
| | 4 | 75• | 135! | 208 Ø | | | | |
| | 5 | 145• | 187 Ø | | | | | |
| | 6 | 145! | 265 Ø | | | | | |
| | 1.5% water | | | | | | | |
| Splitter | 0 | | | | | | | |
| | 2 | 64• | 77• | 118• | 177 Ø | 297 Ø | | |
| | 3 | 72• | | | | | | |
| | 4 | 99• | | | | | | |
| | 5 | 117• | | | | | | |
| | 6 | 157! | | | | | | |

| | | | | Glass | | | | |
|---|---|---|---|---|---|---|---|---|
| IK | | 66 | 67 | 68 | 69 | 70 | 71 | 72 |
| | 0% water | | | | | | | |
| Splitter | 0 | | | 200 Ø | 180 Ø | 139 Ø | 71! | 35! |
| | 2 | 200 Ø | 181 Ø | 144 Ø | 81! | 35! | | |
| | 3 | 178 Ø | | | | | | |
| | 4 | 150 Ø | | | | | | |
| | 5 | 103 Ø | | | | | | |
| | 6 | 74! | | | | | | |
| | 0.5% water | | | | | | | |
| Splitter | 0 | | | | | | | |
| | 2 | 166 Ø | 162 Ø | 112 Ø | 61! | 29• | | |

-continued

|  |  |  |  |  |  |  |
|---|---|---|---|---|---|---|
|  | 3 | 158 Ø | 115 Ø | 57! |  |  |
|  | 4 | 125 Ø | 60! | 28• |  |  |
|  | 5 | 78! | 27• |  |  |  |
|  | 6 | 60! |  |  |  |  |
|  | 1% water |  |  |  |  |  |
| Splitter | 0 |  |  |  |  |  |
|  | 2 | 100! | 87! | 65! | 37! | 22• |
|  | 3 | 73! | 38! | 14• |  |  |
|  | 4 | 58! | 27• | 11• |  |  |
|  | 5 | 45! | 7• |  |  |  |
|  | 6 | 26• | 3• |  |  |  |
|  | 1.5% water |  |  |  |  |  |
| Splitter | 0 |  |  |  |  |  |
|  | 2 | 81! | 46! | 24• | 12• | 4• |
|  | 3 | 55! |  |  |  |  |
|  | 4 | 38! |  |  |  |  |
|  | 5 | 24• |  |  |  |  |
|  | 6 | 11• |  |  |  |  |

|  |  | Glass |  |  |  |  |  |  |
|---|---|---|---|---|---|---|---|---|
| IG/IK |  | 66 | 67 | 68 | 69 | 70 | 71 | 72 |
|  | 0% water |  |  |  |  |  |  |  |
| Splitter | 0 |  |  | 0.3 Ø | 0.5 Ø | 0.8 Ø | 2.8! | 9.6 Ø |
|  | 2 | 0.3 Ø | 0.5 Ø | 0.7 Ø | 2.2! | 8.8 Ø |  |  |
|  | 3 | 0.5 Ø |  |  |  |  |  |  |
|  | 4 | 0.7 Ø |  |  |  |  |  |  |
|  | 5 | 1.4* |  |  |  |  |  |  |
|  | 6 | 2.6! |  |  |  |  |  |  |
|  | 0.5% water |  |  |  |  |  |  |  |
| Splitter | 0 |  |  |  |  |  |  |  |
|  | 2 | 0.3 Ø | 0.4 Ø | 1.0 Ø | 2.7! | 8.3 Ø |  |  |
|  | 3 | 0.4 Ø | 1.0 Ø | 2.7! |  |  |  |  |
|  | 4 | 0.6 Ø | 2.7! | 8.3 Ø |  |  |  |  |
|  | 5 | 1.3* | 8.3 Ø |  |  |  |  |  |
|  | 6 | 2.2! |  |  |  |  |  |  |
|  | 1% water |  |  |  |  |  |  |  |
| Splitter | 0 |  |  |  |  |  |  |  |
|  | 2 | 0.5 Ø | 0.7 Ø | 1.0 Ø | 3.2! | 7.4 Ø |  |  |
|  | 3 | 0.8 Ø | 2.4! | 3.2! |  |  |  |  |
|  | 4 | 1.3* | 5.0* | 7.4 Ø |  |  |  |  |
|  | 5 | 2.3! | 26.7 Ø |  |  |  |  |  |
|  | 6 | 5.6 | 88.3 Ø |  |  |  |  |  |
|  | 1.5% water |  |  |  |  |  |  |  |
| Splitter | 0 |  |  |  |  |  |  |  |
|  | 2 | 0.8 Ø | 1.7* | 4.9* | 14.8 Ø | 74.3 Ø |  |  |
|  | 3 | 1.3* |  |  |  |  |  |  |
|  | 4 | 2.6! |  |  |  |  |  |  |
|  | 5 | 4.9* |  |  |  |  |  |  |
|  | 6 | 14.3 Ø |  |  |  |  |  |  |

Example 3

Influence of Additives with Hydroxy Function (PEG200, Glycerol, MEMO)—Measured Values and Assessments

| | | | | | | | | | | | |
|---|---|---|---|---|---|---|---|---|---|---|---|
| | | | | | Measuring results Textures Analyses | | | | | | |
| Material | | Pre-polymer [%] | Glass [%] | F % | IG Force, g | SD | IK Force, g | SD | Comments | IG | Coefficient IG/IK |
| SOCO GRM | | | | | 130-170 | | 30-100 | | Release range | 130-170 | 1.3-5.67 |
| SOCO GRM VP 250711 Rei | Glycerol | | | | | | | | | | |
| SOCO GRM VP 100811 Rei1 | 0.5% glycerol | 2 | 67 | 69 | 135! | 3 | 87! | 5 | | 135! | 1.6* |
| SOCO GRM VP 100811 Rei2 | 1.0% glycerol | 2 | 67 | 69 | 215 Ø | 4 | 15• | 2 | | 215 | 14.3∞ |
| SOCO GRM VP 110811 Rei1 | 1.5% glycerol | 2 | 67 | 69 | 268 Ø | 6 | 15• | 2 | | 268 | 17.9∞ |
| SOCO GRM VP 250711 Rei1 | 0.5% glycerol | 2 | 69 | 71 | 321 Ø | 6 | 8• | 0.5 | | 321 | 40.1∞ |
| SOCO GRM VP 250711 Rei2 | 1.0% glycerol | 2 | 69 | 71 | 414 Ø | 8 | 6• | 2 | | 414 | 69.0∞ |
| SOCO GRM VP 250711 Rei3 | 1.5% glycerol | 2 | 69 | 71 | 534 Ø | 38 | 10• | 1 | | 534 | 53.4∞ |
| SOCO GRM VP 280711 Rei | PEG 200 | | | | | | | | | | |
| SOCO GRM VP 110811 Rei2 | 0.5% PEG 200 | 2 | 67 | 69 | 87• | 2 | 76! | 6 | | 87 | 1.1∞ |
| SOCO GRM VP 110811 Rei3 | 1.0% PEG 200 | 2 | 67 | 69 | 94• | 2 | 70! | 7 | | 94 | 1.3* |
| SOCO GRM VP 110811 Rei4 | 1.5% PEG 200 | 2 | 67 | 69 | 72• | 3 | 72! | 8 | | 72 | 1.0∞ |
| SOCO GRM VP 280711 Rei1 | 0.5% PEG 200 | 2 | 69 | 71 | 222 Ø | 5 | 30! | 3 | | 222 | 7.4∞ |
| SOCO GRM VP 280711 Rei2 | 1.0% PEG 200 | 2 | 69 | 71 | 171 Ø | 7 | 26• | 3 | | 171 | 6.6∞ |
| SOCO GRM VP 280711 Rei3 | 1.5% PEG 200 | 2 | 69 | 71 | 166! | 1 | 29• | 3 | | 166 | 5.7∞ |
| SOCO GRM VP 250711 Rei | MEMO Silane GF31 | | | | | | | | | | |
| SOCO GRM VP 280711 Rei4 | 0.5% GF31 | 32 | 69 | 71 | 112• | 2 | 150 Ø | 5 | | 112 | 0.7∞ |
| SOCO GRM VP 250711 Rei2 | 1.0% GF31 | | | | no measurements done, too soft | | | | | | |
| SOCO GRM VP 250711 Rei3 | 1.5% GF31 | | | | | | | | | | |
| SOCO GRM VP 140611 KR2/K1 | no H₂O/G 018-053 | 0 | 69 | 69 | 90• | 4 | 180 Ø | 12 | | 90 | 0.5∞ |
| SOCO GRM VP 140611 KR2/K2 | no H₂O/G 018-053 | 0 | 70 | 70 | 118• | 4 | 139 Ø | 9 | | 118 | 0.8∞ |
| SOCO GRM VP 140611 KR2/K3 | no H₂O/G 018-053 | 0 | 71 | 71 | 200 Ø | 3 | 71! | 6 | | 200 | 2.8! |
| SOCO GRM VP 140611 KR2/K4 | no H₂O/G018-053 | 0 | 72 | 72 | 336 Ø | 13 | 35! | 3 | | 336 | 9.6∞ |
| SOCO GRM VP 110811 Rei2 | 0.5% PEG 200 | 2 | 68 | 70 | 158! | 5 | 39! | 3 | | 158 | 4.1! |
| SOCO GRM VP 110811 Rei3 | 1.0% PEG 200 | 2 | 68 | 70 | 143! | 1 | 36! | 3 | | 143 | 4.0! |
| SOCO GRM VP 110811 Rei4 | 1.5% PEG 200 | 2 | 68 | 70 | 151! | 3 | 35! | 2 | | 151 | 4.3* |

Example 3a

Influence of Additives with Hydroxy Function—Matrix Analysis

| | | | | | Glass | | | |
|---|---|---|---|---|---|---|---|---|
| IG | % | | 66 | 67 | 68 | 69 | 70 | 71 | 72 |
| | | % glycerol | | | | | | | |
| Splitter | 0 | | | | | 90• | 118• | 200 Ø | 118• |
| | 2 | 0.5 | | 135! | | 321 Ø | | | |
| | 2 | 1.0 | | 215 Ø | | 414 Ø | | | |
| | 2 | 1.5 | | 268 Ø | | 534 Ø | | | |
| | | % PEG 200 | | | | | | | |
| Splitter | 0 | 0 | | | | 90• | 118• | 200 Ø | 336 Ø |
| | 2 | 0.5 | | 87• | 158! | 222 Ø | | | |
| | 2 | 1.0 | | 94• | 143! | 171 Ø | | | |
| | 2 | 1.5 | | 72• | 151! | 166! | | | |
| | | % Silane GF31 | | | | | | | |
| Splitter | 0 | | | | | 90• | 118• | 200 Ø | 336 Ø |
| | 2 | 0.5 | | | | 112• | | | |
| | 2 | 1.0 | | | | | | | |
| | 2 | 1.5 | | | | | | | |

-continued

| IK | % | | Glass | | | | | | |
|---|---|---|---|---|---|---|---|---|---|
| | | | 66 | 67 | 68 | 69 | 70 | 71 | 72 |
| | % glycerol | | | | | | | | |
| Splitter | 0 | | | | | 180 Ø | 139 Ø | 71! | 35! |
| | 2 | 0.5 | | 87! | | 8• | | | |
| | 2 | 1.0 | | 15• | | 6• | | | |
| | 2 | 1.5 | | 15• | | 10• | | | |
| | % PEG 200 | | | | | | | | |
| Splitter | 0 | 0 | | | | 180 Ø | 139 Ø | 71! | 35! |
| | 2 | 0.5 | | 76! | 39! | 30! | | | |
| | 2 | 1.0 | | 70! | 36! | 26• | | | |
| | 2 | 1.5 | | 72! | 35! | 29• | | | |
| | % Silane GF31 | | | | | | | | |
| Splitter | 0 | | | | | 180 Ø | 139 Ø | 71! | 35! |
| | 2 | 0.5 | | | | 112 Ø | | | |
| | 2 | 1.0 | | | | | | | |
| | 2 | 1.5 | | | | | | | |

| IG/IK | % | | Glass | | | | | | |
|---|---|---|---|---|---|---|---|---|---|
| | | | 66 | 67 | 68 | 69 | 70 | 71 | 72 |
| | % glycerol | | | | | | | | |
| Splitter | 0 | | | | | 0.5 Ø | 0.8 Ø | 2.8! | 9.6 Ø |
| | 2 | 0.5 | | 1.6• | | 40.1 Ø | | | |
| | 2 | 1.0 | | 14.3 Ø | | 69.0 Ø | | | |
| | 2 | 1.5 | | 17.9 Ø | | 53.4 Ø | | | |
| | % PEG 200 | | | | | | | | |
| Splitter | 0 | 0 | | | | 0.5 Ø | 0.8 Ø | 2.8! | 9.6 Ø |
| | 2 | 0.5 | | 1.1 Ø | 4.1! | 7.4 Ø | | | |
| | 2 | 1.0 | | 1.3• | 4.0! | 6.6 Ø | | | |
| | 2 | 1.5 | | 1.0 Ø | 4.3• | 5.7 Ø | | | |
| | % Silane GF31 | | | | | | | | |
| Splitter | 0 | | | | | 0.5 Ø | 0.8 Ø | 2.8! | 9.6 Ø |
| | 2 | 0.5 | | | | 0.7 Ø | | | |
| | 2 | 1.0 | | | | | | | |
| | 2 | 1.5 | | | | | | | |

The invention claimed is:

1. Method for adjusting or improving or optimizing the usage properties of filler(s)-containing, flowable dental material, to which
   i) at least one pre-polymer filler A1 is added;
   ii) the fraction of component A1 is varied;
   iii) at least one hydroxy function-containing additive A2 with a molecular weight <250 g/mol is added whereby additive A2 is represented through formula H—Y—Z (I) where:
   Y=—O—, —S—, —CO—, —OSi(OR$^1$)$_2$—, —OE
   Z=H, OH, SH, NH$_2$, COOH, COOR$^2$
   E=—C$_n$H$_m$O$_p$—
   R$^1$=H, C$_1$-C$_4$-Alkyl
   R$^2$=C$_1$-C$_{15}$-Alkyl, interrupted by one or more O atoms, C$_2$-C$_{14}$-Alkyl,
   n=2-5
   m=4-11
   p=n;
   iv) measuring a value IK (Force, g) representing the tackiness and measuring a value IG (Force, g) representing the texturing or plasticity or consistency are related to each other
   whereby the IG value representing the texturing/plasticity/consistency is determined from the requisite force upon passage through a defined constriction or from the opposing force at a predetermined penetration depth of a measuring stamp, and/or
   whereby the value IK presenting the tackiness is determined from the peeling force required to peel a measuring stamp, which has been pressed onto the sample with a defined force, off the surface of the composite; and
   v) an optimized ratio of at least one glass filler and pre-polymer filler is determined;
   whereby the ratio of the IG value representing the texturing/plasticity/consistency divided by the tackiness value IK is used as a measuring parameter for assessment of the quality and;
   vi) the IG/IK ratio of the dental material is adjusted to from at least 1.3 to at most 5.6.

2. Method according to claim 1, which comprises adding the at least one compound represented by formula H—Y—Z (I) in amounts of 0.1 to 5% by weight of the total composition.

3. Method according claim 1, wherein, in addition, the quantitative ratio of pre-polymer filler and glass filler(s) is varied.

4. Method according to claim 1, wherein additive A2 is represented through formula H—Y—Z(I), wherein formula (I) represents water, polyethylene glycol (PEG) of MG<250, glycerol and glycol.

5. Method according to claim 1, wherein the dental material is a composite containing the following components:
   65 to 75% by weight glass filler
   optionally 1 to 5% pre-polymer filler
   0.1 to 5% by weight additive represented through formula H—Y—Z(I)
   15 to 25% by weight monomer mixture,
   15 to 20% by weight crosslinker.

6. Method for determining optimized usage properties of flowable, filler(s)-containing dental composites wherein the optimized dental composites comprise at least one hydroxy function-containing additive A2 with a molecular weight<250 q/mol represented through formula H—Y—Z (I) where:
   Y=—O—, —S—, —CO—, —OSi(OR$^1$)$_2$—, —OE
   Z=H, OH, SH, NH$_2$, COOH, COOR$^2$
   E=—C$_n$H$_m$O$_p$—
   R$^1$=H, C$_1$-C$_4$-Alkyl
   R$^2$=C$_1$-C$_{15}$-Alkyl, interrupted by one or more O atoms, C$_2$-C$_{14}$-Alkyl,
   n=2-5
   m=4-11
   p=n,
   including the steps of
   A) determining a value IK (Force, g) representing the tackiness whereby the value IK representing the tackiness is determined from the peeling force required to peel a measuring stamp, which has been pressed onto the sample with a defined force, off the surface of the composite;
   B) determining a value IG (Force, g) representing the texturing or plasticity or consistency; whereby the IG value representing the texturing/plasticity/consistency is determined from the requisite force upon passage through a defined constriction or from the opposing force at a predetermined penetration depth of a measuring stamp,
   C) calculating the ratio, IG/IK, whereby the ratio of the IG value represents the texturing/plasticity/consistency divided by the tackiness value IK wherein said ratio is used as measuring parameter for assessment of the quality and wherein said ratio is from at least 1.3 to at most 5.6.

7. Method according to claim 6, wherein additive A2 is represented through formula H—Y—Z(I), wherein formula (I) represents water, polyethylene glycol (PEG) of MG<250 and glycerol, wherein compounds represented through formula H—Y—Z (I) are used to optimize the usage properties, where:
   Y=—O—, —S—, —CO—, —OSi(OR$^1$)$_2$—, —OE
   Z=H, OH, SH, NH$_2$, COOH, COOR$^2$
   E=—C$_n$H$_m$O$_p$—
   R$^1$=H, C$_1$-C$_4$-Alkyl
   R$^2$=C$_1$-C$_{15}$-Alkyl, interrupted by one or more O atoms, C$_2$-C$_{14}$-Alkyl,
   n=2-5
   m=4-11
   p=n.

8. Filler(s)-containing, flowable dental material treated according to claim 1, wherein the fillers comprise at least one glass filler selected from silanized dental glass and at least one filler A1 selected from the group consisting of chipped polymers or pre-polymer fillers based on ground polymer that is pre-polymerized together with inorganic particles and further comprise at least one compound represented through formula H—Y—Z (I) in amounts of 0.1 to 5% by weight of the total composition, where:
   Y=—O—, —S—, —CO—, —OSi(OR$^1$)$_2$—, —OE
   Z=H, OH, SH, NH$_2$, COOH, COOR$^2$
   E=—C$_n$H$_m$O$_p$—
   R$^1$=H, C$_1$-C$_4$-Alkyl
   R$^2$=C$_1$-C$_{15}$-Alkyl, interrupted by one or more O atoms, C$_2$-C$_{14}$-Alkyl,
   n=2-5
   m=4-11
   p=n,
   wherein the IG/IK value of the dental material is in the range of from at least 1.3 to at most 5.6.

9. Dental material according to claim 8, wherein the inorganic particles comprise silicon dioxide.

10. Dental material according to claim 8, having an IG/IK value of 2-5.

11. Dental material according to claim 8, wherein the IG/IK value is in the range of 2 to 3.

12. Dental material treated according to claim 1, containing
   65 to 75% by weight glass filler selected from the group consisting of BaAl silicate glass,
   0.1 to 5% by weight additive represented by formula H—Y—Z (I)
   15 to 25% by weight monomer mixture,
   15 to 20% by weight cross-linker
   wherein the IG/IK value of the dental material is in the range of 1.3 to 5.6.

13. Method of claim 6 for improving the usage properties of flowable fillers containing dental composites, which comprises adding at least one compound represented by formula H—Y—Z (I),
   where:
   Y=—O—, —S—, —CO—, —OSi(OR$^1$)$_2$—, —OE
   Z=H, OH, SH, NH$_2$, COOH, COOR$^2$
   E=—C$_n$H$_m$O$_p$—
   R$^1$=H, C$_1$-C$_4$-Alkyl
   R$^2$=C$_1$-C$_{15}$-Alkyl, interrupted by one or more O atoms, C$_2$-C$_{14}$-Alkyl,
   n=2-5
   m=4-11
   p=n
   to said dental composites in amounts of 0.1 to 5% by weight, relative to the total composition.

14. Composition according to claim 12, further comprising 1 to 5% chipped polymer.

15. Method according to claim 1, which comprises adjusting the IG/IK value of said dental materials to 2-5.

16. Method according to claim 7, wherein the IG/IK ratio of the optimized dental material is between 2 and 5.

* * * * *